US011642058B2

(12) United States Patent
Curtiss

(10) Patent No.: US 11,642,058 B2
(45) Date of Patent: *May 9, 2023

(54) SYSTEM AND METHOD FOR MEASURING REACTION TIME OF A SUBJECT

(71) Applicant: SWAY MEDICAL, INC., Tulsa, OK (US)

(72) Inventor: Chase Curtiss, Tulsa, OK (US)

(73) Assignee: SWAY MEDICAL, INC., Tulsa, OK (US)

( * ) Notice: Subject to any disclaimer, the term of this patent is extended or adjusted under 35 U.S.C. 154(b) by 750 days.

This patent is subject to a terminal disclaimer.

(21) Appl. No.: 16/520,421

(22) Filed: Jul. 24, 2019

(65) Prior Publication Data

US 2019/0343440 A1 Nov. 14, 2019

Related U.S. Application Data

(63) Continuation of application No. 14/504,285, filed on Oct. 1, 2014, now Pat. No. 10,362,977.

(60) Provisional application No. 61/885,278, filed on Oct. 1, 2013.

(51) Int. Cl.
*A61B 5/16* (2006.01)
*A61B 5/00* (2006.01)
*A61B 5/11* (2006.01)

(52) U.S. Cl.
CPC .......... *A61B 5/162* (2013.01); *A61B 5/6898* (2013.01); *A61B 5/1121* (2013.01)

(58) Field of Classification Search
CPC ...... A61B 5/162; A61B 5/6898; A61B 5/1121
See application file for complete search history.

(56) References Cited

U.S. PATENT DOCUMENTS

| 2012/0330178 A1* | 12/2012 | Kraft | A61B 5/378 |
| | | | 600/544 |
| 2013/0035613 A1* | 2/2013 | Curtiss | A61B 5/4023 |
| | | | 600/595 |

* cited by examiner

*Primary Examiner* — Alex M Valvis
*Assistant Examiner* — Yasmeen S Warsi
(74) *Attorney, Agent, or Firm* — Fellers, Snider, Blankenship, Bailey & Tippens, P.C.; Terry L. Watt

(57) ABSTRACT

There is provided herein a motion-based evaluation of reaction time that utilizes motion detection hardware of a mobile device to determine auditory and visual stimulated reaction time. In an embodiment, the subject holds a mobile computing device equipped with built-in triaxis accelerometer and gyroscope with both hands at arms length away from the face. A visual or auditory stimulus is then presented on screen via a software application that also records the response time for the individual to initiate a movement of the device. A simple reaction time test could include the movement of the device in any direction that exceeded a threshold of movement beyond what would be expected from static holding. An embodiment of a choice reaction time test would provide for specific directional movements as it related to an instructed stimulus.

15 Claims, 2 Drawing Sheets

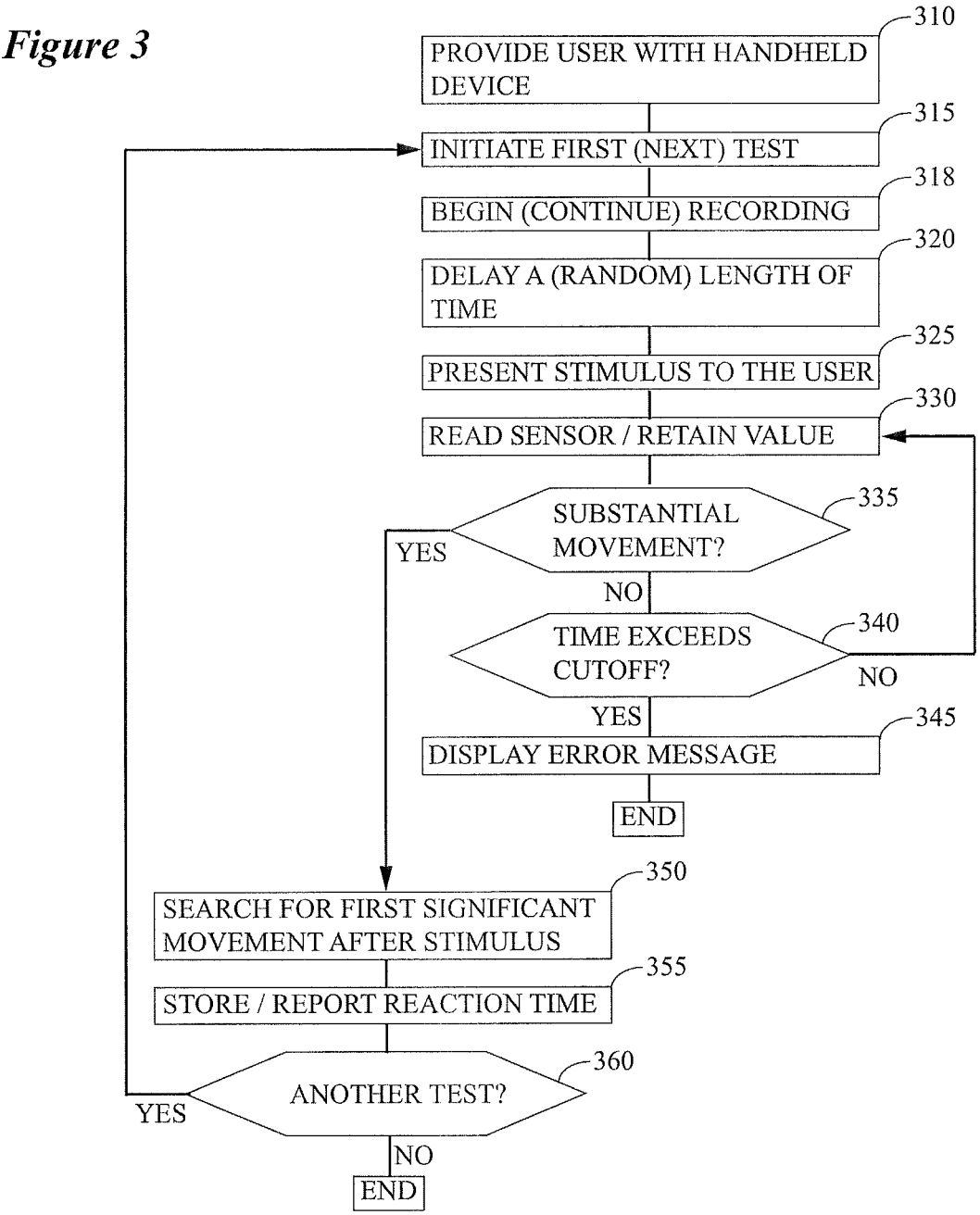

SYSTEM AND METHOD FOR MEASURING REACTION TIME OF A SUBJECT

CROSS REFERENCE TO RELATED APPLICATIONS

This application is a continuation of co-pending U.S. utility patent application Ser. No. 14/504,285, filed Oct. 1, 2014, and claims the benefit of U.S. Provisional Patent Application Ser. No. 61/885,278 filed on Oct. 1, 2013, and incorporates said utility and said provisional applications by reference into this document as if fully set out at this point.

FIELD OF THE INVENTION

The present invention relates generally to the field of cognitive and neuropsychological assessment.

BACKGROUND OF THE INVENTION

The development of more portable assessment techniques of cognitive and vestibular characteristics has been well documented by researchers and innovators. Techniques for assessing subject memory, reasoning, discrimination, intellect, etc., using mobile devices have been developed. However, reaction time has not shown consistent measures. The high variability in mobile device touch-screen based reaction time testing presents a problem for accurate assessment of reaction time that is not typically seen with desktop/laptop computer-based approaches that record reaction time with mouse clicks or pressing a key such as the space bar.

Reaction time is a measure of sensory and neuromotor function that encompasses stimulus recognition and processing followed by the initiation of a neuromotor response. Reaction time can be tested with varying levels of difficulty in the sensory phase, or the neuromotor response phase. The Simple Reaction Time (SRT) test is the most elementary form of reaction time measurement, which looks at signal processing of a single stimulus with a defined physical response, such as pressing a button.

Reaction time is typically evaluated digitally via a computer program running on a desktop computer, which measures the time lapse between stimulus presentation on the screen and the touch of a keyboard or click of a mouse. More practical and accessible tools for reaction time assessment have been suggested, however these tools are typically not digitally connected for archiving individualized comparative measurements and require equipment that is not always available outside of the clinic.

Computerized testing is generally accepted as the gold standard for reaction time assessment. Inherent in the reaction time measurement is a time lag (latency) between the time a key is depressed and when it is registered by the computer. Computerized testing remains popular despite mouse and keyboard latency variations of 20 to 50 milliseconds between commercially available models. Additionally, a practical limitation of computerized testing is the immobility of the testing platform.

Recent efforts to promote cognitive assessment on mobile devices have attempted to address the portability issue in computerized testing with the use of touch screen devices such as cell phones. A transition to touch screen reaction time assessment has been slowed due to latency in the touch identification mechanisms of mobile devices Recent studies have failed to produce statistical equivalence between touch-based reaction time assessment and computerized testing.

More concerning is the latency caused by delays between the time when a user's finger contacts a touch screen and the time that contact is registered by the CPU. This can introduce inaccuracies into measured reaction time values. In some cases, depending on the hardware and software resident within the mobile device, the latency might be between 20 and 100 milliseconds (i.e., between about 0.020 and 0.100 seconds). With average human simple reaction time scores of 230 ms, and standard deviation of 20 ms, the current touch screen latency does not provide a medium for accurate measures. A small sample of neurocognitive testing on a mobile device showed slower and more variable measurements of response times when compared against computerized models. There remains a critical need for more accurate reaction time measures on touch-screen portable computing devices.

Additionally, user experience inconsistencies in the touching action with variability of initial finger distance from the screen create inconsistencies in accurately measuring response time. Distance of the finger from the screen had a significant effect on reaction time score. Additional use cases have been presented where the user begins with screen contact and removes the finger as a capture of response to stimulus. This action has an improved accuracy of reaction time score, but still contends with the scanning rate of the run loop and screen input latency.

In short, the technical translation of touch screen reaction time detection to this point may fail to accurately measure reaction time in both simple and choice reaction time trials.

As such there has been, and remains, a critical need for more accurate reaction time measures on touch-screen portable computing devices.

Heretofore, as is well known in the cognitive testing industry, there has been a need for an invention to address and solve the disadvantages of prior art methods. Accordingly it should now be recognized, as was recognized by the present inventors, that there exists, and has existed for some time, a very real need for a system and method that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of the invention within the ambit of the appended claims.

SUMMARY OF THE INVENTION

According to an embodiment there is provided a motion-based evaluation of reaction time that utilizes the motion detection hardware of a mobile device to determine auditory and visual stimulated reaction time.

In one embodiment, the subject will hold a mobile computing device equipped with built-in triaxis accelerometer and/or gyroscope with both hands at arms length away from the face. A visual or auditory stimulus will then be presented on screen via a software application that records the response time for the individual to initiate a movement of the device. In one embodiment the acceleration of the device will be continuously measured from an onset time until after a substantial movement is recorded post-presentation of the stimulus. Then, the continuously recorded acceleration curve will be searched to determine the earliest intentional movement in the same axis as the substantial movement that broke a given threshold after presentation of the stimulus. The time difference between the presentation of the stimulus and the earliest intentional movement will be a measure of reaction time.

Another embodiment will continuously monitor the gyroscope in the handheld device from an onset time until after a substantial change in orientation is sensed. As in the previous embodiment, after the change is sensed the earliest intentional change will be identified and the time of such change noted. The time difference between the presentation of the stimulus and the time of the first intentional orientation change will then be used as a measure of reaction time.

As a further example, a simple reaction time test could include the movement of the device in any direction that exceeded a threshold of movement beyond what would be expected from static holding. An embodiment of a choice reaction time test would provide for specific directional movements as it related to an instructed stimulus.

The foregoing has outlined in broad terms the more important features of the invention disclosed herein so that the detailed description that follows may be more clearly understood, and so that the contribution of the instant inventors to the art may be better appreciated. The instant invention is not limited in its application to the details of the construction and to the arrangements of the components set forth in the following description or illustrated in the drawings. Rather the invention is capable of other embodiments and of being practiced and carried out in various other ways not specifically enumerated herein. Additionally, the disclosure that follows is intended to apply to all alternatives, modifications and equivalents as may be included within the spirit and the scope of the invention as defined by the appended claims. Further, it should be understood that the phraseology and terminology employed herein are for the purpose of description and should not be regarded as limiting, unless the specification specifically so limits the invention.

BRIEF DESCRIPTION OF THE DRAWINGS

Other objects and advantages of the invention will become apparent upon reading the following detailed description and upon reference to the drawings in which:

FIG. 3 contains an operating logic suitable for use with an embodiment.

DETAILED DESCRIPTION

The present invention, in one embodiment, is a software application running on a mobile device that is equipped with an accelerometer and, in some embodiments, a gyroscope. Readings from the device when then provide data that measures elements of cognitive function based on motion response. One software application measures simple and choice reaction time which might be initiated by, for example, presenting the user with a stimulus such as turning the entire screen to the color red, and timing a response to initiate movement. Another reaction time test presents the user with arrows that indicate the direction to move the device, as well as associative relationships with colors, which present an added level of cognitive function to recall color association. As with any reaction time test, the user is indicated that the stimulus will be presented and a one to four second fore period precedes the actual presentation of the stimulus.

The present invention, according to one embodiment, is a software application that runs on a mobile device that measures elements of cognitive function based on motion response. The motion response is quantified, for example, using an accelerometer and/or gyroscope that is integral to the mobile device. Simple and choice reaction time can be measured by presenting the user with a stimulus such as turning the entire screen to the color red, and timing a response to initiate movement. An example of a choice reaction time test would present the user with arrows in the direction to move the device, as well as associative relationships with colors, which would present an added level of cognitive function to recall color association. As with any reaction time test, the user will be notified that the stimulus is to be presented and a one to four second fore period will precede the actual presentation of the stimulus.

Figure 1:
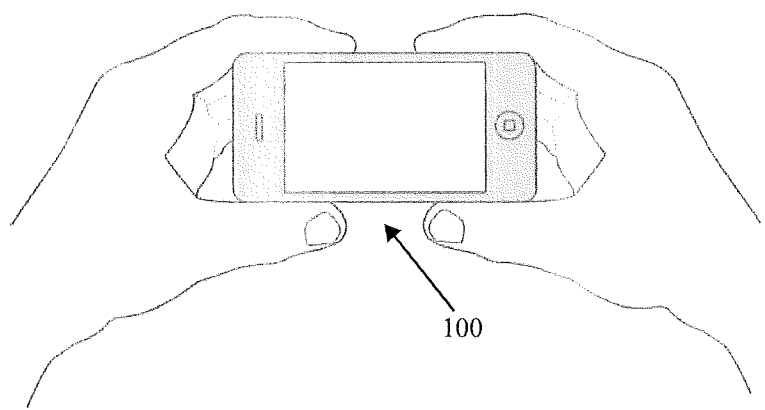
FIG. 1 contains an illustration of a general environment of an embodiment of the invention.

Turning first to FIG. 1, there is provided a method of measuring reaction time by executing a program on a portable computing device such as a cell phone 100. According to an embodiment, the device 100 will contain an accelerometer and use motion of the device to assess access reaction time as discussed below.

Figure 2:
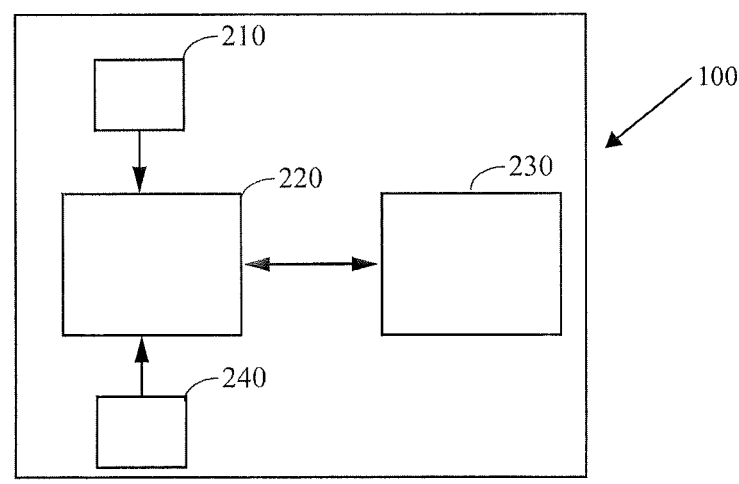
FIG. 2 contains a hardware schematic of an embodiment.

FIG. 2 contains a schematic illustration of a hardware configuration that would be suitable for use with an embodiment 100. In the embodiment of this figure, the portable device 100 will contain an accelerometer 210 and/or a gyroscope 240 that are in electronic communication with a CPU 220. Not shown is some amount of memory (volatile and/or nonvolatile) that would be useful in connection with the software embodiment of the instant disclosure. Additionally, there will typically be provided a device such as a LED or other display device 230 which could be used to communicate information to a user. The interconnection between the CPU 220 and the display device 230 is shown to be bidirectional because, in some embodiments, the display device might be a touch-sensitive display and the CPU 220 might be programmed to obtain information from the user via the display 230.

Note that one potential use for the display device 230 would be to initiate a response time test (e.g., by changing color, flashing, printing a "START" or other text message, etc.). That being said those of ordinary skill in the art will recognize that a test could be initiated in any number of other ways including, for example, sounding an audible tone, vibrating the device (e.g., using the vibration mode of a phone), etc. Although some embodiments will be based on an Apple iPhone® that is not a requirement and any device that that can be hand held or worn on the body (such as a wrist watch or glasses) and that contains an accelerometer or gyroscope could potentially be utilized.

The CPU 220 might be within the same enclosure as the accelerometer 210 or in electronic communication with it (either wired or wireless). Multiple CPUs might be involved as would be the case where a multicore device is used (e.g., where different functions are handled by different cores), or where separate CPUs that are in electronic communication with each other.

One function of the CPU 220 is continuously read the accelerometer 210 from a time before the start of the test until after a response is identified or until after a predetermined period of time has passed. Note that for purposes of the instant disclosure when the word "continuously" is used herein, that usage should be understood to mean that an operation is performed repeatedly during some period of time. For example, if a quantity is said to be continuously measured during some time period, that could mean that the quantity is measured every second, every 0.1 seconds, every 0.01 seconds, etc., with the measurements spacings being dependent on the length of the time period and context in which the term appears. Additionally, it should be noted that the operations (measurements in the current example) need not be equally spaced throughout the measurement period but only that they should be spaced apart. Thus, and by way of example only, in one embodiment "continuously" will mean nominally performed 500 to 1000 times a second, i.e., at intervals of 1 to 2 milliseconds, where the actual spacing between successive measurements might vary about the nominal value. Those of ordinary skill in the art will recognize that the sampling interval might be longer or shorter than this and selecting such will be will within the ability of one of ordinary skill in the art.

In one embodiment the accelerometer 210 will be a three-component (triaxis) accelerometer. In some embodiments both an accelerometer 210 and a gyroscope 240 will be present in the same device.

Turning next to FIG. 3, this figure contains an operating logic suitable for use with an embodiment. With respect to box 310, as an initial step the test subject will be provided with a hand-held device suitable for use with the methods taught herein and instructed in its use. More particularly, in many embodiments this will be an iPhone® or other cellular telephone on which a computer program that is designed to perform the operations described below in connection with the current embodiment. Of course, it is not required that a telephone be used. All that is required is that the device contains a CPU (to include any programmable device such as microprocessor, micro controller, programmable gate array, etc.) that is in electronic communication with a module that can sense movement and/or orientation of the device.

Note that, in some embodiments, the user might be asked to hold the device with as little movement as possible for a period of time to establish a baseline stability curve. It should be clear that some individuals will be able to hold the test device relatively motionless whereas others, for physical or other reasons, might have more difficulty doing this. As such, it might be useful to establish a baseline stability (e.g., the average acceleration during the calibration time) before collecting data. The baseline stability could then be used in connection with the determination of substantial/significant movement thresholds discussed hereinafter.

In one embodiment, the test subject will be instructed to hold the device in a landscape orientation with both hands on the device as is suggested by the example of FIG. 1 on which software which is designed at least in part to implement an embodiment of the methods taught herein has been preloaded. Clearly, if the software has not been preloaded in some variations in might be downloaded to the device via a wireless or wired connection. The user will then be asked to presses "Begin Test" (step 315) or provide some similar indicium to the recording device to indicate that s/he is ready to begin testing. In some embodiments, this will signal the beginning of the onset time, the time during which the motion of the device will be recorded.

Next, according to some embodiments the sensor that is responsible for determining motion of the device will be continuously read and saved for a period of time to be described below (step 318), where continuously should be understood to take the meaning ascribed to it herein. In some embodiments, the sample interval for such continuous sampling might be 1 or 2 milliseconds. In some embodiments, the accelerometer or other device responsive to motion will be read at 1 or 2 millisecond intervals by the instant invention according to methods well known to those of ordinary skill in the art, each such reading producing at least one value representative of motion.

Note that in embodiments that utilize a three-component accelerometer, each reading from such a device might result in three values: acceleration in each of an X, Y, and, Z direction with respect to the device. In some embodiment, the three units of motion that might be read from such a device will be combined into a single/composite value representative of the overall motion of the device in some embodiments. In other instances, one or more components of acceleration might be used. For example, in some embodiments only the vertical component of acceleration might be used. In some embodiments (e.g., where the user has not held the device in a perfectly horizontal position initially) it might be necessary to numerically extract the vertical component of acceleration from the three-component values that are read from the accelerometer, e.g., if the subject has been asked to move the device vertically in response to the stimulus. No matter how it is determined, for purposes of example and discussion only it will be assumed that a single value that is representative of the motion of the device has been obtained that can be used to indicate motion of the device.

As has been discussed previously, although some embodiments of the invention utilize a sensor in the form of an accelerometer or gyroscope to sense motion, it should be understood that these devices have been given by way of example only and not of limitation. For example, a digital camera could also function as a motion sensor either, for example, by using the anti-shake feature of the camera to sense motion or by using the field of view of the camera (e.g., by requiring the user to point the camera at a static image, e.g. a target, and noting the changes in the camera's field of view). That being said, an accelerometer or gyroscope would generally provide better results. Additionally, an embodiment uses multiple of the above (e.g., both an accelerometer and a gyroscope) to sense motion. One motion source could be used as a check against the other or the measurements could be combined and utilized as follows.

A randomly selected fore period can be used to prevent anticipation of the stimulus (step 320). Although this time interval might be randomly selected it also could be selected deterministically depending on the needs of the supervising user. Clearly, the measurements might be called into question if there were a pattern in a repeated presentation of a stimulus or if the timing were such that it could be accurately anticipated.

Next in some embodiments a stimulus will be presented to the user (step 325). The stimulus might take many forms. In some embodiments the stimulus will be presented by printing a text message on the screen, changing the color of the screen, flashing the handheld devices camera flash, etc. In other instances, an audible tone or vibration of the device might be utilized as the stimulus.

After the stimulus has been presented, the sensor will be repeatedly read (330) and retained in memory until either a substantial movement is noted (step 335) or until the elapsed time exceeds some predetermined value (e.g., 1, 2, 3, 5, 10, etc., seconds, step 340). In some embodiments, a substantial movement will be a movement that exceeds a predetermined threshold. Note that, in some embodiments, rather than finding the first single value that exceeds the movement threshold, some number of sequential measurements that exceed that value might be required (e.g., 2, 3, 5 or more, etc.) before a substantial movement is identified. In the event that the movement sensor is an accelerator, the movement threshold might be the time at which a value greater than or equal to 0.1 g is sensed. Clearly, other thresholds could be chosen by those of ordinary skill in the art.

One purpose for the timeout is to accommodate those instances where a user abandons the test after indicating a readiness to take it. In that case, an error message might be displayed (step 345) and the routine terminated. However, in some embodiments the "YES" branch of decision item 340 might branch directly to step 350 instead of ending the routine. This might be useful if there is a high noise level, if it is suspected that a predetermined ending time would always include the significant movement, etc. In that instance, the substantial movement time could be set equal to the predetermined ending time and the method continued as described below.

If, after the onset of the test, a substantial movement has not been detected and the timer has not expired, a new value will be read from the sensor (step 330). The value that is read will be stored or otherwise retained for subsequent use.

Once the movement exceeds a predetermined threshold (the "YES" branch of decision item 335), an embodiment will search through the recorded motion readings since the onset and find the first time a significant motion occurs.

Figure 4:
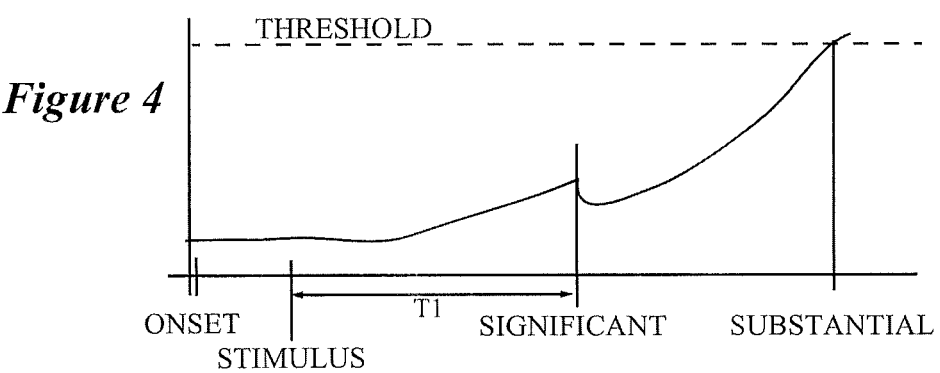
FIG. 4 contains a schematic illustration of a response time curve.

Once the time of the earliest significant movement is determined, the response time can be calculated as the elapsed time since the presentation of the stimulus ("T1" in FIG. 4). FIG. 4 contains a schematic representation of how a motion response curve might appear. Typically, the response time will be immediately communicated to the test administrator (e.g., via WiFi or Bluetooth) and/or accumulated and reported at the end of the testing procedure (e.g., when the device is handed back to the administrator). The individual curves themselves might be communicated to the test administrator or not depending on the preferences of the software designer and/or the test administrator.

Finally, in some embodiments one or more additional tests will be performed (the "YES" branch of decision item 360). As a specific example, in some embodiments each user will be asked to perform five tests which will be averaged together or otherwise combined to produce a single representative value. In some instances, the fastest and slowest reaction times might be dropped before the average or other combination is calculated. Additionally, it may be useful to save and report the standard deviation (or other measure of variability) of the recorded scores. The final response score or scores (including, or not, the raw data curves) will be communicated to the test administrator By way of one specific example, according to one embodiment a key to motion response will be to determine an appropriate level of allowable motion, yet adding sensitivity to the detection of intentional motion. The potential variation in measures of many accelerometers of the sort found in handheld devices when held perfectly stationary might range from 0.02 g's to 0.025 g's. In addition, since in some embodiments the user will be holding the device in front of his or her body (e.g., as in FIG. 1), this can lead to added motion beyond resting at a static state. Various threshold and data collection frequency values can be used, for illustrative purposes the current embodiment assigns the following values:

Threshold: 0.1 g

Data Collection Frequency: 1000 hz

Reaction Measure: Stimulus to first accelerating value preceding threshold.

In practice an embodiment might be implemented as follows. The subject will be instructed to hold a mobile computing device equipped with built-in triaxis accelerometer and gyroscope with both hands at arms length away from the face. A visual or auditory stimulus is then presented on screen via a software application that records the response time for the individual to initiate a movement of the device beyond an established threshold. A reaction time test includes the movement of the device in any axis that breaks a threshold of movement with an analysis of acceleration immediately prior to breaking the threshold to determine when intentional motion had been initiated. One embodiment stores the acceleration values as an array to allow for a reverse analysis of acceleration data points to determine when acceleration started in the direction of intentional movement, determined by breaking the threshold.

The following method of reaction time testing is a particular example of how a test might be performed in practice:

1. The user will be instructed that when a stimulus is presented (e.g., the screen color will change from white to orange), the device should be shaken or moved.

2. After the user indicates a readiness to participate by pressing a "Begin Test" or similar on-screen button, a one to four second fore-period or delay (which might be randomly selected) before the stimulus is presented will be used to reduce the likelihood the user will be able to anticipate the stimulus.

3. The stimulus will be presented to the user.

4. The accelerometer or other motion sensor will be continuously read. The start time for the reading could be the moment the stimulus is presented, sometime before that, or a time shortly after its presentation. In some embodiments values read from the motion sensor before the presentation of the stimulus might be used to calculate a baseline movement level. For purposes of this example, if the motion sensor is an accelerometer the values that are read and/or quantities numerically obtained from such readings will be stored in an array $A(\cdot)$, where $A(\cdot)$ contains values that are representative of the motion of the device during the recording period. Note that $A(\cdot)$ might actually be a multidimensional array (e.g., $A(\cdot,\cdot)$, $A(\cdot,\cdot,\cdot)$, etc.) where the quantities representative of motion are multidimensional.

5. Once the stimulus appears, the user will move the device quickly to exceed the motion threshold (substantial movement).

6. The point at which the threshold is broken will denominated as data point N, where N corresponds to the sample number within the $A(\cdot)$ array at which the measured acceleration is greater than 0.1 g, and where "g" is the acceleration due to gravity.

7. The acceleration values leading up to N will have been recorded at 1000 hz (1 ms time intervals) and stored in the array $A(\cdot)$ for analysis.

8. A query will then be then performed on the acceleration sample points prior to N to determine if acceleration was occurring and when acceleration began (i.e., a search will be conducted for the first "significant movement"). Numerically, this amounts to checking the stored acceleration or other values representative of motion, A(i), N, in reverse time order:

Query: Is data point $A(N-1)<A(N)$?

If yes, then is $A(N-2)<A(N-1)$?, etc.

9. The previous query will continue until is the test is False (i.e., $A(i-1) \geq A(i)$). At that point, in this example the algorithm will have determined the earliest moment of intentional acceleration in response to the stimulus and reaction time is recorded.

10. Five trials will be repeated to ensure consistency.

Of course, in some instances the data array might be subsampled (to reduce its sample rate), or interpolated (to increase its effective sample rate). It might also be frequency filtered (e.g., a high pass, low pass, or band pass), subjected to a running average, edited to remove spikes (e.g., via a median filter), etc. Those of ordinary skill in the art will recognize that any number of numerical algorithms might be applied to the data to increase its signal-to-noise ratio and make it more conducive to analysis.

Additionally, it should be noted that tests that include True/False, or Go/No-Go could be administered. This embodiment might provide more precise motion recognition of the response which can be superior to the less sensitive touch and voice responses. As an example, in order to perform the True/False function, the user might be instructed to move left for false and right for true, then be presented with a question to assess their cognitive ability. The correctness of the response would be recorded, as well as the response time to initiate the response movement. A Go/No-Go test could be performed by the same sort of motion capture physics as previously described, with a No-Go response being indicated by a one second period of stillness below the 0.005 g threshold.

In an embodiment the threshold level could also be calibrated per user based on tremor of that individual. As an example, a familiarization trial with a set fore-period of 3 or 4 seconds would allow the user to better learn the testing process without actual data collection, while the mobile software recorded a baseline tremor level that could be used to customize the threshold level for that user or as a separate neurological assessment.

Generally speaking, embodiments of the instant invention, operating as they do on familiar handheld devices such as an iPhone® or a similar handheld computing device, can eliminate the need for the sort of high cost equipment that is conventionally used in motion based reaction assessment. Embodiments of the instant invention provide a unique and proprietary approach to a combined unit of stimulus presentation (audio and visual), measurement and computation with high quality sensors that are already built into the device. This approach to motion based capture of reaction time and cognitive function on a portable computing device provides a much more accurate way to measure cognitive function.

Finally, it should be noted and remembered that what is most useful in one embodiment is determining the earliest time at which voluntary movement of the handheld device is sensed after the stimulus is presented to the test subject. A method for doing that using motion sensors that are integral to or within a handheld device is taught herein. Other methods of sensing such motion may readily be devised by those of ordinary skill in the art.

It should be noted that if reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is also to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention ☐is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof; selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%.

When, in this document, a range is given as "(a first number) to (a second number)" or "(a first number)–(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

While this invention is susceptible of embodiment in many different forms, there is shown in the drawings, and is herein described in detail, some specific embodiments. It should be understood, however, that the present disclosure is to be considered an exemplification of the principles of the invention and is not intended to limit it to the specific embodiments or algorithms so described. Those of ordinary skill in the art will be able to make various changes and further modifications, apart from those shown or suggested herein, without departing from the spirit of the inventive concept, the scope of which is to be determined by the following claims.

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Additionally, it should be noted that when an operation is said to be performed in "real time", that phrase should be understood to mean that the operation is performed proximate to the time it is requested as opposed to operations that occur at a much later time. By way of example, adjustment of a parameter in real time during a sweep should be understood mean the adjust takes place during the sweep and not after its completion.

Further, it should be noted that when the term "access" is used in connection with data acquired by a seismic survey that term should be understood to mean reading via a computer seismic data that is stored on a volatile or non-volatile medium. The seismic data acquired during a survey contains signals that are representative of the configuration of the earth proximate to the survey and may or may not have been previously treated with some number of computer algorithms to improve its usability at the time it is accessed. In the event that the term "access" is applied to synthetic or generated seismic data, that usage should be understood to mean that the data so-accessed has been created based on the interaction of computer algorithms that are programmed to utilize the physics of transmission, reflection, diffraction, etc., with a hypothetical model of the earth proximate to some area of interest.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those skilled in the art, without departing from the spirit of the inventive concept the scope of which is to be determined by the following claims.

What is claimed is:

1. A method of measuring a reaction time of a subject, comprising the steps of:
   (a) providing a handheld computing device to the subject, said handheld computing device having a motion sensor integral thereto;
   (b) instructing the subject to hold the handheld computing device motionless until after a stimulus has been presented and then to move the handheld computing device in response to the stimulus as quickly as possible after the stimulus has been presented;
   (c) selecting a movement threshold value;
   (d) presenting the stimulus to the subject at a stimulus time;
   (e) within said handheld computing device, continuously reading digital values from the motion sensor from said stimulus time at least until a time when a read digital value exceeds said movement threshold value, thereby reading a plurality of digital values;
   (f) determining from said plurality of digital values an earliest time of an intentional movement of said handheld computing device at a time between said stimulus time and said time when said read digital value exceeds said movement threshold value; and
   (g) determining the reaction time of the subject to be a time difference between said stimulus time and said earliest time of said intentional movement.

2. The method according to claim 1, wherein said motion sensor is continuously read at intervals of 0.001 seconds or 0.002 seconds.

3. The method according to claim 1, wherein said motion sensor is selected from the group consisting of an accelerometer and a gyroscope.

4. The method according to claim 1, wherein said motion sensor is an accelerometer and said movement threshold value is greater than or equal to an acceleration value of 0.1 g.

5. The method according to claim 1, wherein said motion sensor is a triaxis accelerometer, wherein each of said continuously read digital values from the motion sensor comprises three acceleration values corresponding to acceleration in an X, a Y, and a Z direction, and wherein step (f) comprises the steps of:
   (f1) for each of said plurality of read digital values, forming a composite acceleration value from said accelerations in said X, said Y, and said Z directions, thereby creating a plurality of composite acceleration values; and
   (f2) determining from said plurality of composite acceleration values said earliest time of said intentional movement of said handheld computing device at said time between said stimulus time and said time when said read digital value exceeds said movement threshold value.

6. The method according to claim 1, wherein said motion sensor is an accelerometer and wherein step (f) comprises the steps of:
   (f1) searching through said plurality of digital values backward in time from said time when said read digital value exceeds said movement threshold value toward said stimulus time to find a first instance where, as between two adjacently digital values, an earlier measured one of said two adjacently digital values is greater than a later one of said two adjacently digital values, thereby determining an earliest time of an intentional movement.

7. The method according to claim 1, wherein the handheld digital computing device has a display integral thereto and wherein step (d) comprises the step of presenting the stimulus to the subject at the stimulus time using said display.

8. The method according to claim 1, further comprising the step of:
   (h) using said handheld computing device to report said reaction time of the subject.

9. A method of measuring a reaction time of a subject, wherein the subject is provided with a handheld computing device containing a motion sensor integral thereto, comprising the steps of:
   (a) instructing the subject to hold the handheld computing device motionless until after a stimulus has been presented and then to move only the handheld computing device in response to the stimulus as quickly as possible after the stimulus has been presented;
   (b) selecting a movement threshold;
   (c) using the handheld computing device to present a stimulus to the subject at a stimulus time;
   (d) within the handheld computing device, continuously reading a plurality movement values from the motion sensor from said stimulus time until a first time when at least one of said plurality of movement values exceeds said movement threshold, said first time at which said at least one of said plurality of movement values exceeds said movement threshold comprising a first substantial movement time;

(e) determining within said handheld computing device from said start time, said first substantial movement time, and said plurality of movement values a first intentional movement time after said start time and before said first substantial movement time;

(f) determining within said handheld computing device said reaction time of the subject to be a time difference between said first intentional movement time and said start time; and (g) using said handheld computing device to report said reaction time.

10. The method according to claim 9, wherein said motion sensor is read at intervals of 0.001 seconds or 0.002 seconds.

11. The method according to claim 9, wherein said motion sensor is selected from the group consisting of an accelerometer and a gyroscope.

12. The method according to claim 9, wherein said motion sensor is an accelerometer and said movement threshold is 0.1 g.

13. The method according to claim 9,
wherein said motion sensor is a triaxis accelerometer,
wherein each of said continuously read plurality of movement values comprises three acceleration values corresponding to acceleration in an X, a Y, and a Z direction, and wherein step (e) comprises the steps of:

(e1) for each of said plurality of movement values, forming a composite acceleration value from said X, said Y, and said Z direction accelerations;

(e2) determining within said handheld computing device from said start time, said first substantial movement time, and said plurality of composite acceleration values a first intentional movement time after said start time and before said first substantial movement time.

14. A method of measuring a reaction time of a subject, comprising the steps of:

(a) providing a handheld computing device to the subject, said handheld computing device having a motion sensor integral thereto, wherein said motion sensor comprises a triaxis accelerometer;

(b) instructing the subject to hold the handheld computing device motionless until after a stimulus has been presented and then to move the handheld computing device in response to the stimulus as quickly as possible after the stimulus has been presented;

(c) selecting a movement threshold value;

(d) presenting the stimulus to the subject at a stimulus time;

(e) within said handheld computing device, continuously reading digital values from the motion sensor from said stimulus time at least until a time when a read digital value exceeds said movement threshold value, thereby reading a plurality of digital values, each of said continuously read digital values from the motion sensor comprising three acceleration values corresponding to acceleration in an X, a Y, and a Z direction;

(f) for each of said plurality of read digital values, forming a composite acceleration value from said accelerations in said X, said Y, and said Z directions, thereby creating a plurality of composite acceleration values;

(g) determining from said plurality of composite acceleration values an earliest time of an intentional movement of said handheld computing device at a time between said stimulus time and said time when said read digital value exceeds said movement threshold value; and (g) determining the reaction time of the subject to be a time difference between said stimulus time and said earliest time of said intentional movement.

15. The method according to claim 14, wherein step (g) comprises the steps of:

(g1) searching through said plurality of composite acceleration values backward in time from said time when said read digital value exceeds said movement threshold value toward said stimulus time to find a first instance where, as between two adjacently digital values, an earlier measured one of said two adjacently digital values is greater than a later one of said two adjacently digital values, thereby determining an earliest time of an intentional movement.

* * * * *